United States Patent [19]
Garwood et al.

[11] 3,985,128
[45] Oct. 12, 1976

[54] PHOTOCURABLE CONTOUR CONFORMING SPLINT

[75] Inventors: Donald C. Garwood, Malibu; Harry Taw, El Toro, both of Calif.

[73] Assignee: Merck & Co., Inc., Rahway, N.J.

[22] Filed: June 2, 1975

[21] Appl. No.: 583,122

[52] U.S. Cl. ................................................. 128/90
[51] Int. Cl.$^2$ .......................................... A61F 5/04
[58] Field of Search ................ 128/90, 89, 87, 156; 161/89, 93

[56] References Cited
UNITED STATES PATENTS

| | | | |
|---|---|---|---|
| 3,421,501 | 1/1969 | Beightol | 128/90 |
| 3,787,272 | 1/1974 | Nisbet et al. | 128/90 X |
| 3,881,473 | 5/1975 | Corvi | 128/90 |

FOREIGN PATENTS OR APPLICATIONS

| | | | |
|---|---|---|---|
| 121,007 | 4/1971 | Norway | 128/90 |

*Primary Examiner*—John D. Yasko
*Attorney, Agent, or Firm*—Harry E. Westlake, Jr.; Rudolph J. Anderson, Jr.

[57] ABSTRACT

A splint which can be trimmed to the size and shape of a limb and molded to the latter's contours is prepared by impregnating a knit or woven fabric of specific dimensions with a photocurable resin and, after trimming and molding, setting the whole into a strong rigid splint of perfect fit. The product has many advantages, including air and water permeability, rigidity even when wet, easily dried, etc., over splints previously known.

12 Claims, No Drawings

PHOTOCURABLE CONTOUR CONFORMING SPLINT

This invention relates to an orthopedic splint moldable to the contours of the limb and then capable of being hardened to a method of splinting a limb by molding a plastic coated fiberglass support to the contour of a limb, hardening the same by exposure to light of the proper wavelength and then binding them on the limb.

BACKGROUND OF THE INVENTION

In the past, splints have been made from a variety of materials, chiefly plaster, metal and plastic. Splints, in terms of duration of use, are of three types: emergency splints, short term splints and medium to long term splints. Emergency splints are temporary in use; their primary objective is to immobilize an injured part while x-rays are taken and are usually in place only a few hours. Short-term splints are often used until swelling of an injured limb subsides after which the limb may be enclosed in an orthopedic cast. The period of use of a short term splint generally is from 2 to 5 days. Since the duration of use of emergency and short-term splints is limited, the splints need not be especially durable. Such splints usually are made of plaster of paris, which although not strong and durable is inexpensive.

Long term splints, because of the need for durability, are made of materials such as metals, plastic coated metals (aluminum, for example), and thermoforming plastics. There are two categories of such splints: preformed to a general shape of a limb and moldable splints that can be shaped to conform exactly to the patient's limb. Pre-formed splints do not generally conform exactly to an individual patient's limb resulting in a poor fit that is uncomfortable for the patient and may not be adequately immobilize, support and protect the injured member. The moldable splints while more conformable are not as rigid and strong as pre-formed splints. Some moldable materials are rendered flexible by heating and while hot can be molded into a variety of shapes and so conform well. However, they lack strength, are expensive and require considerable time to cut, trim and mold. Devising splints from these materials requires considerably skill in the use of wood and metal working tools, high temperature ovens, heat guns, hot water baths, solvents, and grinding tools. Generally the skills and equipment needed call for the services of an orthotist and a fully equipped appliance room. Cast rooms are not equipped to work with such materials.

Other moldable splints have been reported. In most cases these are dependent on solvents to soften the stiffening agent and after molding the solvent must be evaporated. Since most of these solvents are flammable, there is a constant fire hazard. In many cases, solvents useable can be toxic upon contact with the skin and this too is a deficiency. A further deficiency is that the evaporation of the solvent is necessarily a very slow process.

Another form of contour splint depends on a thermosetting resin. Such resins are usually two component systems involving the monomer and catalytic polymerization agent. It is necessary in order to use these resins to mix the two components, coat the splint while molded to the contours of the limb and then polymerize by the use of heat. Not only is this process slow but the use of heat is a limitation since the polymerization must be done on the limb.

Photocurable materials are on the market for use in casts, as described by Beightol U.S. Pat. No. 3,421,501 and Corvi et al. U.S. Pat. No. 3,881,473. In these casts a tape impregnated with a photosensitive resin system is wrapped around the limb. Rigidity is obtained by the laminating effect of winding the tape in several layers. The Corvi modification achieved a quicker cure by controlling the size of the openings in the tape in order to permit light penetration through the various layers. For a splint, it is necessary to have a limited amount of lamination in order to permit moldability, easy and fast curing and ability to trim the splint to conform in size to the limb. Thus, one cannot use the tape used to make casts. In order to get rigidity, these need a multilayer application. When used in single or even double layers, little or no rigidity is obtained.

THE PRESENT INVENTION

We have found that it is proper to use the photo-curing technique in the preparation of splints by using a fabric which is at least 0.05 inches thick and having less than 80% of its space as openings or windows in the thread, the said fabric being impregnated with a photocurable resin until there is 30 to 60% of the total weight as resin. Such a material produces a splint which is easily moldable to the contour of the limb, easily trimmable with a pair of scissors and after curing has the desired rigidity.

ADVANTAGES OF THE INVENTION

It is an advantage of this invention that it is very easily molded. It is either unlaminated or at the most used in a double layer and is therefore not too thick to prevent such easy molding when in an uncured state. Unlike the case of laminated tapes used in casts, there is no problem of the nonalignment of interstices which has the effect of slowing the cure. This ability to produce a completely perfect contour is the biggest advantage over preformed splints which have been used in an attempt to get an approximation of the limb contour.

It is a further advantage of this invention that a splint is obtained having great strength and rigidity. Thermoplastic splints are easily warped by body heat or the general heat of the surrounding air but the splints of this invention are very rigid, both essential properties for use as a splint.

It is a further advantage of this invention that the splint can be shaped and trimmed by scissors to fit the exact size of the limb to be supported. Laminations of casting tape, which might produce sufficient rigidity, cannot be so trimmed.

It is a still further advantage of this invention that the splints have a large degree of porosity and air permeability, both properties contributing immensely to the comfort of the wearer.

A further advantage of this invention is that the splints are impervious to water and rapidly dry. Thus, the wearer is not inhibited in normal activities such as washing, showering and even swimming. Nor are the wearers subject to the sweating and the lack of cleanliness normally associated with an old fashioned splint, through which no air could penetrate.

FABRICS USED IN THIS INVENTION

In the production of the splints of this invention, it is preferred that the fabrics be fiberglass filaments twisted and plied into yarns of varying construction and then knitted. Of special preference is a laid-in Raschel knit in which the front yarn guide bar executes a chain stitch while the remaining bars perform laps to lay in additional reinforcing yarn and to tie together the chain stitches across the courses. In such a knit the yarn material is preferably fiberglass of filament size C (fiber diameter ranges from $15 \times 10^{-5}$ inches to $20 \times 10^{-5}$ inches) with a "singles" strand of fibers yielding a linear length of 15,000 yards per pound. After being knitted, all fiberglass fabrics must be cleaned by heating in the air of an oven at a temperature of 760° F. for periods of time long enough to insure combustion of impurities (typically 5 hours).

More important than the specific fiber in the case of knitted fabrics is the yarn of which it is constructed and the knit or weave which is used. The fabric for the splint of this invention will vary in the proportion of its surface which is open space depending on the above factors. However, no more than 80% of the total surface may be open space or interstices. Preferably the open space should constitute between 15 and 25% of the total surface.

In order to obtain the rigidity needed in this invention, the fabric should have a density no more than 1.0 square yards per pound. With higher areas per pound, there is insufficient material in the fabric to give the rigidity needed for proper support of an injured limb. In any case, the minimum thickness needed to give the proper density and rigidity is 0.05 inches. Thinner fabrics will not have sufficient rigidity after cure to support the injured limb. The rigidity is tested by the following test:

The samples are made in the form of hardened (3 minutes in Light Source A) laminates 3 inches in width and 6 inches long. Each sample is supported in a horizontal plane by two parallel knife-edges spaced 4 inches apart. A load is applied to a third knife-edge positioned over the center of the laminate, 2 inches from each of the supporting knife edges and parallel to them. The loads reported are an average of 6 determinations made on separate samples of each type. The loads correspond to peak loads at which the deflection was about ½ inch.

In the following examples, five fabrics are compared. These fabrics are as follows:

FABRIC A

Fabric A is a fiberglass material knitted on a Raschel machine having a gauge of 9 (corresponding to a needle spacing to give 4½ needles per inch of needle bed width). The fabric is knitted in 3 and 4 inch wide strips, with 17 wales in the 3 inch width and 22 wales in the 4 inch width, has a thickness of approximately 0.046 inches, a fabric density of 1.7 square yards per pound, and is quite porous with approximately 3/16 inch square openings separating adjacent wales and filling laps. Details of Fabric A construction are given in the accompanying table.

| Guide Bar | Fabric A Construction | | Yarn Construction** |
|---|---|---|---|
| | Lapping Motion* | Threading | |
| Bar 1 | (2-0/0-2), chain stitch | 1 end per guide needle | 2/2 |
| Bar 2 | (0-0/2-2/0-0/4-4/2-2/4-4) | 1 end per guide needle | 2/4 |
| Bar 3 | (0-0/2-2) | 1 end per guide needle | 2/6 |

*The repeating segment of pattern chain links describes the lapping motion.
**Designation shows the number of "singles" strands twisted together/number of such twisted strands plied together.

FABRIC B

Fabric B construction is identical to Fabric A except that 2 ends of 2/4 fiberglass yarn are threaded through each guide needle of bar 2, and 3 ends of 2/6 yarn are used in each guide needle of bar 3. The fabric is consequently much heavier and has more reinforcing yarn incorporated into its structure. The fabric is knitted in both 3 inch and 4 inch wide strips, has a thickness of approximately 0.065 inches, a fabric density of 0.8 square yards per pound, and is similar to Fabric A in its open structure.

FABRIC C

The construction of Fabric C is also the same as Fabric A except that a synthetic polyester yarn (Dacron type 52 manufactured by E. I. Dupont de Nemours & Co.) is used instead of fiberglass as follows:
bar 1: 1 end per guide of 440 denier
bar 2: 2 ends per guide of 1100 denier
bar 3: 3 ends per guide of 1100 denier
The resulting fabric has a thickness of approximately 0.048 inches, a fabric density of 2.5 square yards per pound, and an openness comparable to Fabric A. It has a width of 3 inches.

FABRIC D

Fabric D is a fiberglass fabric knitted with a finer needle gauge than the previous three fabrics to produce smaller sized openings, to incorporate more material per fabric surface area for strength, and to obtain a smoother feeling fabric. The needle spacing gives 9 needles per inch of knitting width (18 gauge Raschel). The fabric is knitted in a 3 inch wide strip and possesses 32 wales. The fabric construction is explained in the accompanying table. The material is 0.065 inches thick (as in Fabric B), has a fabric density of 0.50 square yards per pound and has openings of approximately 1/16 inch square.

| Guide Bar | Fabric D Construction | | Fiberglass Yarn |
|---|---|---|---|
| | Lapping Motion* | Full Set Threading | |
| Bar 1 | chain stitch | 1 end | 2/2 |
| Bar 2 | (0-0/4-4) | 1 end | 2/6 |
| Bar 3 | (0-0/2-2) | 2 ends | 2/6 |
| Bar 4 | (0-0/2-2) | 2 ends | 2/6 |

FABRIC E

Fabric E is identical in construction to Fabric D except that guide bar 2 is caused to lap across four needles, i.e. the lapping motion of bar 2 is (0-0/8-8). This is done to increase the strength of the fabric in the fill direction (across the wales). The thickness is 0.079 inches with a fabric density of 0.39 square yards per pound. The size of openings is about 1/32 of an inch square.

LIGHT SOURCES

The light sources used to cure or harden the splints of this invention can be either visible or ultraviolet light. Which is to be used is determinative of the initiator which is incorporated in the resin composition. Such initiators are disclosed in the Beightol and Corvi patents mentioned above or in the South African patent to Dart et al., No. 72/8004. In general, initiators which are sensitive to visible light will also be sensitive to ultraviolet light whereas those initiators sensitive to ultraviolet light are not necessarily sensitive to visible light.

In the examples which follow, two light sources are used described as follows:

LIGHT SOURCE A

Light Source A consists of sixteen 24 inch long fluorescent tubes arranged axially along the inside wall of a 18 inch diameter cylindrical reflector. The light spectrum is in the near ultraviolet region, with the major emission between 350nm and 400nm, a peak intensity at 367nm, and a light intensity over this spectral range of about 12 milliwatts per square centimeter in the center of the cylindrical region.

LIGHT SOURCE B

The primary difference between Light Source A and B is that the latter produces light in the blue part of the visible spectrum. Light Source B consists of two 48 inch long, 1½ inch diameter fluorescent tubes manufactured by General Electric and designated as F40 SPB/5 Super Blue housed in a polished aluminum reflector. The reflector consists of two parallel V-shaped sections (72° angle) such that the tubes are spaced 6 inches apart. The tubes are powered by two General Electric fluorescent tube ballasts (designated 8G1000) connected in parallel. A reasonably uniform light intensity is obtained in a central position about 5 inches from the tubes.

POLYMERS

Thirty to 60 percent by total weight of the resin impregnated fabric which constitutes the splint before curing must be a photocurable polymer. Examples of such polymers can be found disclosed in Beightol U.S. Pat. No. 3,421,501, Corvi et al. U.S. Pat. No. 3,881,473 and Dart et al. South African Pat. No. 72/8004. Such disclosures are expressly incorporated herein by reference.

In the following examples the resins used were prepared as follows:

RESIN A

Vinyltoluene (manufactured by the Dow Chemical Co. and designated Vinyltoluene-50T) (6.98 liters), a solution of 5.76 g. of 4-tert-butylcatechol in 25 ml. of acetone, and 7 liters of acetone are placed in the water jacketed mixing tank of a high shear mixer (manufactured by Myers Engineering, Inc., Bell, CA). While stirring 22.5 kg. of a powered unsaturated polyester is added gradually. This polyester is the condensation product of a one-to-one mole ratio of isophthalic acid and maleic anhydride with 1,2-propylene glycol and has an acid number less than 14, a melting point above 77° C., and a viscosity when dissolved in methyl cellosolve to yield a 60% by weight solution of Y to Z at 25° C. on the Gardner viscosity scale. Mixing is continued with occasional interruptions to allow cooling so that the temperature remains below 50° C. until all the polyester is dissolved. Finally, a solution of 346 g. of benzoin methyl ether in 875 ml. of acetone is added and thoroughly mixed with the resin solution.

RESIN B

Toluhydroquinone (4.0 g.) is dissolved in 500 g. of diethyl fumarate. Vinyltoluene (manufactured by Dow Chemical Co. and designated as Vinyltoluene-50T) (5.6 liters) and the above solution are stirred in a high shear mixer while 12.2 kg. of a powdered unsaturated polyester (identical to that used in resin A) is added. When a complete solution is obtained 300 g. of benzoin isobutyl ether is mixed into the solution.

RESIN C

Vinyltoluene (220 g.), 0.16 g. of 4-t-butylcatechol, and 560 g. of unsaturated polyester (identical to that used in Resins A and B) are mixed in a Waring blender by intermittent stirring and cooling. The time required to obtain a complete solution is approximately 1 hour. Then a solution of 16.0 g. of benzoin methyl ether dissolved in 20 g. of vinyltoluene is mixed with the resin.

RESIN D

Vinyltoluene (120 g.), 16 g. of N,N-dimethylaminoethyl methacrylate, and 256 g. of the unsaturated polyester (described above for Resin A) are blended together in a Waring blender. Benzil (8.0 g.) is dissolved by blending in the resin.

Our invention can be illustrated by the following examples:

EXAMPLE 1

Fabric A is coated with Resin A by passing both materials together through a gap of 0.025 inches between two rollers and then passing the resin coated fabric through an oven heated to 140° F. to evaporate the acetone. The fabric is wet with 45% by weight of resin. A single layer of the resin impregnated fabric is applied to the anterior surface of the forearm and palm of the hand and shaped to fit. While in place on the arm, the material is hardened by a couple minutes exposure to Light Source A. The cured structure is insufficiently rigid and does not adequately support the member when attached with straps. However, when 4 or 5 layers of the resin impregnated fabric are laminated together prior to shaping on the patient and curing, improved rigidity is achieved. Additional time is required and inconvenience incurred to prepare the laminated fabric before applying it to the patient. Also, the exposure time to the light to harden the splint is excessive (6 minutes or more) due to the greater thickness of the splint.

EXAMPLE 2

To reduce the inconvenience of forming multilayered laminates and to reduce the light exposure time to harden the material, a heavier fabric of pattern similar to that of Example 1 is desired. Consequently, Fabric B is impregnated with Resin A as described in Example 1. Although with one layer, the material is too flexible for use as a splint, two layers are quite rigid. The laminates formed of this material could be cured in less time (3 minutes) than the materials of similar rigidity of Example 1.

EXAMPLE 3

The materials of Example 1 and Example 2, because of the wide spacing of wales and the large openings have rough surfaces and require padding between them and the patients skin to avoid abrasion. Fabric C, although of similar structure, because of replacement of fiberglass by a synthetic textile after coating with Resin A diluted with acetone (1 part acetone to 4 parts resin) provides a smoother surface on the finished splint. However, large numbers of laminate layers (more than 5 in almost all instances) and long curing exposures of 10 to 15 minutes are required to build splints with a moderate degree of immobilizing rigidity.

EXAMPLE 4

To overcome the requirement to make laminates prior to use of the material and to improve surface smoothness, Fabric D having closer spaced wales is impregnated with Resin B to obtain a material containing 44.2% resin by weight and is then formed into a splint. A single layer of cured material provides sufficient rigidity. The material hardens well upon a 3 minute exposure to Light Source A, and the surface is much smoother to the touch than the first two examples. It is also found that while the hardened splint has good strength in the direction of the wales, the hardened fill yarns fracture easily so that the splint would tear lengthwise.

EXAMPLE 5

A more quantitive evaluation of the rigidity provided by the above examples is given in Table 1 in which the load required to deflect each material is compared. The test used has been described above.

TABLE 1

| | | | Rigidity of 3 Inch Wide Splints | | | | |
| | | | Deflection Load, pounds of force for various laminates | | | | |
| Example | Fabric | Resin Amount | 1 Layer | 2 Layers | 3 Layers | 4 Layers | 5 Layers |
| --- | --- | --- | --- | --- | --- | --- | --- |
| Example 1 | A | 45.0% | approx. 0 | 4.5 | 29.2 | 60 | 105 |
| Example 2 | B | 43.5% | 2.6 | 45.5 | 139 | — | — |
| Example 3 | C | 55.3% | — | — | — | 37 | 53 |
| Example 4 | D | 44.2% | 26 | 178 | — | — | — |

EXAMPLE 6

Fabric E, possessing more fill yarn for crosswise strength, is impregnated with 44.9% by weight of Resin C by use of a two roller coater. The resin impregnated material was found to conform well to the contours of body members, hardens within 3 minutes upon exposure to Light Source A, and is strong and rigid in both lengthwise and crosswise directions. It is as smooth to the touch as Example 4. The load required to deflect a 6 inch long, 4 inch wide hardened strip is shown in Table 2. A single layer in this size (4 inches by 6 inches) weighs only 42 grams.

TABLE 2

| | | Rigidity of 4 Inch Wide Splints | | | |
| | | Resin Amount, % by weight | Deflection Load, pounds/force | | |
| Example | Fabric | | 1 Layer | 2 Layers | 4 Layers |
| --- | --- | --- | --- | --- | --- |
| Example 1 | A | 47.8% | — | 6 | 77 |
| Example 6 | E | 44.9% | 36* | 282 | — |
| Example 7 | — | — | 15** | — | — |
| Example 8 | E | 44.9% | 35* | 254 | — |
| Example 9 | E | 41.3% | — | 121 | — |

*The deflection was about ⅞ inch at peak load sustaining ability.
**Deflected ⅞ inch.

EXAMPLE 7

For comparison, a commercially available thermoplastic splint of the same dimensions as Example 6 weighed 70 grams, considerably more than Example 6, but had less rigidity (Table 2).

EXAMPLE 8

The hardened material of Example 6 is immersed for 15 minutes in a water bath maintained at 45° C. to simulate conditions encountered in bathing, hydrotherapy, and similar water exposure to which the splint may be subjected in use. As shown in Table 2 the strength and rigidity remained essentially unchanged.

EXAMPLE 9

To show that an alternate light spectrum and resin composition can be employed in this type of splint, Fabric E is impregnated with Resin D. The resulting material is formed into a splint and is then hardened by exposure to Light Source B for 3 minutes. The splint is adequately strong and rigid although less so than Example 6. The rigidity of a 2 layer laminate is shown in Table 2 for comparison with other examples.

EXAMPLE 10

The utility of the invention has been amply demonstrated by responses from clinical trials. Several different hospital orthopedic clinics were provided with 4 inches × 15 inches Splint Kits that included web wrap and velcro straps. The splints were applied to 8 male and 3 female patients. Applications included treatment of wrist drop (cock-up splint), sprained wrist (volar splint), and tendon involvement (finger splint). Other categories of use were protective, support, and immobilization. Users evaluated the overall utility of the splint on a scale of "poor", "fair", "good" or "excellent". Six splints were considered "excellent" in utility; the other five were classed "good".

We claim:

1. An orthopedic splint capable of being conformed to the contours of a limb and hardened in place which comprises not more than two layers of fabric coated with a photocurable polymer composition, said fabric being at least 0.05 inches thick, having a density such that a pound covers a maximum of one square yard, and having no more than 80 percent of its surface as openings between threads, said polymer composition comprising 30 to 60 percent by weight of said splint.

2. A splint of claim 1 in which said fabric is fiberglass.

3. A splint of claim 2 in which the fabric is a knit fabric.

4. A splint of claim 3 in which the fabric is a laid-in Raschel knit.

5. A splint of claim 4 in which there is only one layer of fabric.

6. A splint of claim 5 in which the polymer composition is curable by ultraviolet light.

7. A method of splinting a limb for orthopedic purposes which comprises 1. placing upon said limb a moldable splint, said splint comprising not more than two layers of fabric coated with a photocurable polymer composition, said fabric being at least 0.05 inches thick, having a density such that a pound covers a maximum of one square yard, and having no more than 80 percent of its surface as openings between threads, said polymer composition comprising 30 to 60 percent by weight of said splint;

2. molding said splint to the exact contours of said limb, trimming its size and dimensions as necessary;

3. curing said splint by exposure to a light source; and 4. binding said splint to said limb.

8. The method of claim 7 in which the fabric in said splint is fiberglass.

9. The method of claim 8 in which the fabric in said splint is a knit fabric.

10. The method of claim 9 in which the fabric is a laid-in Raschel knit.

11. The method of claim 10 in which the splint comprises only one layer of fabric.

12. The method of claim 11 in which the light used to cure is ultraviolet light.

* * * * *

UNITED STATES PATENT OFFICE
CERTIFICATE OF CORRECTION

PATENT NO. : 3,985,128
DATED : October 12, 1976
INVENTOR(S) : Donald C. Garwood & Harry Taw It is certified that error appears in the above-identified patent and that said Letters Patent are hereby corrected as shown below:

Column 1, line 7 - After the word "hardened" and before the word "to" add the following: "in place by exposure to light. Further, it relates".

Column 1, line 38 - Delete the word "be".

Column 1, line 46 - Delete the word "considerably" and in its place add the word "considerable".

Signed and Sealed this

Eighth Day of February 1977

[SEAL]

Attest:

RUTH C. MASON
Attesting Officer

C. MARSHALL DANN
Commissioner of Patents and Trademarks